United States Patent
Murphy, Jr. et al.

(10) Patent No.: US 6,543,276 B2
(45) Date of Patent: Apr. 8, 2003

(54) OIL WELL BORE HOLE FILTER CAKE BREAKER FLUID TEST APPARATUS AND METHOD

(75) Inventors: Robert J. Murphy, Jr., Kingwood, TX (US); Dale E. Jamison, Humble, TX (US); Brad Todd, Duncan, OK (US)

(73) Assignee: Halliburton Energy Services, Inc., Duncan, OK (US)

( * ) Notice: Subject to any disclaimer, the term of this patent is extended or adjusted under 35 U.S.C. 154(b) by 0 days.

(21) Appl. No.: 09/861,362

(22) Filed: May 18, 2001

(65) Prior Publication Data

US 2003/0029230 A1 Feb. 13, 2003

(51) Int. Cl.⁷ .................. G01N 15/04; G01N 17/00; E21B 49/10
(52) U.S. Cl. .................. 73/61.63; 73/865.6; 73/152.25
(58) Field of Search ............... 73/61.63, 61.64, 73/865.6, 152.25

(56) References Cited

U.S. PATENT DOCUMENTS

| | | | | | |
|---|---|---|---|---|---|
| 3,864,970 | A | * | 2/1975 | Bell | 73/152.25 |
| 4,430,889 | A | * | 2/1984 | Sutton | 73/147 |
| 4,528,842 | A | * | 7/1985 | Brown | 73/61.63 |
| 4,538,452 | A | * | 9/1985 | Hrvojic | 73/61.64 |
| 4,548,080 | A | * | 10/1985 | Sweet | 73/865.6 |
| 4,748,849 | A | | 6/1988 | Jamison et al. | 73/61.4 |
| 6,055,874 | A | * | 5/2000 | Onan et al. | 73/865.6 |
| 6,269,684 | B1 | * | 8/2001 | Maki, Jr. et al. | 73/53.01 |

OTHER PUBLICATIONS

Burton, R. C.: "Estimate Formation Damage Effects on Horizontal Wells," Pet. Eng. Intl. (Aug. 1995), 29–34.
Burton R. C. and Hodge, R.M.: "The Impact of Formation Damage and Completion Impairment on Horizontal Well Productivity," paper SPE 49097, presented at the 1998 SPE Annual Technical Conference and Exhibition, New Orleans, Sep. 27–30.
Ryan, D. F., Browne, S.V., and Burnham, M.P.: "Mud Clean–Up in Horizontal Wells: A Major Joint Industry Study," paper SPE 30528, presented at the 1995 SPE Annual Technical Conference and Exhibition, Dallas, Oct. 22–25.
Gilchrist, J. M.: Sutton, L. W., Jr., and Elliott, F. J.: "Advancing Horizontal Well Sand Control Technology" An OHGP Using Synthetic OBM, paper SPE 48976, presented at the 1998 SPE Annual Technical Conference and Exhibition, New Orleans, Sep. 27–30.

(List continued on next page.)

Primary Examiner—Helen Kwok
Assistant Examiner—Jay L Politzer
(74) Attorney, Agent, or Firm—Craig W. Roddy; Karen B. Tripp (57) ABSTRACT

A method and apparatus for determining the effectiveness and reaction time of a breaker fluid in breaking a filter cake on the wall of a wellbore penetrating a subterranean formation is disclosed. The method comprises employing an apparatus, such as for example the apparatus of the invention with a filter medium and the capability of applying differential pressure or dynamic conditions to form a filter cake on the filter medium with drilling mud. Breaker fluid is then substituted for the drilling mud, preferably without damage to the filter cake. The quantity of breaker fluid passing across the filter medium under static conditions is monitored over time. An increase in the rate of fluid passing across or through the medium indicates break-up of the filter cake.

23 Claims, 6 Drawing Sheets

OTHER PUBLICATIONS

Alfenore, J. Longeron, D., and Saintpere, S.: "What Really Matters in our Quest of Minimizing Formation Damage in Open Hole Horizontal Wells," paper SPE 54732, presented at the 1999 SPE European Formation Damage Conference, The Hague, The Netherlands, May 31–Jun. 1.

McLarty, J. M., Dobson, J. W., and Dick, M. A.: "Overview of Offshore Horizontal Drilling/Completion Projects Unconsolidated Sandstones in the Gulf of Mexico," paper OTC 7352, presented at the 1993 Annual OTC, Houston, May 3–6.

Browne, S. V. and Smith, P. S.: "Mudcake Cleanup to Enhance Productivity of High–Angle Wells," paper SPE 27350, presented at the 1994 SPE International Symposium on Formation Damage Control, Lafayette, Louisiana, Feb. 7–10.

Hodge, R. M. et al.: "Evaluation and Selection of Drill–in Fluid Candidates to Minimize Formation Damage," paper SPE 31082, presented at the 1996 International Symposium on Formation Damage Control, Lafayette, Louisiana, Feb. 14–15.

Hale, A. H. et al.: "Selection and Qualification of Drill–in Fluids for Horizontal Wells in Unconsolidated Sands," paper SPE 37077, presented at the 1996 International Conference on Horizontal Well Technology, Calgary, Alberta, Canada, Nov. 18–20.

Burnett, D. B. and Hodge, R. M.: "Laboratory and Field Evaluation of the Role of Drill Solids in Formation Damage and Reduced Horizontal Well Productivity," paper SPE 37125, presented at the 1996 SPE International Conference on Horizontal Well Technology, Nov. 18–20.

Lau, H. C. and Davis C. L.: "Laboratory Studies of Plugging and Clean–Up of Production Screens in Horizontal Wellbores," paper SPE 38638, presented at the 1997 SPE Annual Technical Conference and Exhibition, San Antonio, Texas, Oct. 5–8.

Burnett, D. B.: "Wellbore Cleanup in Horizontal Wells: An Industry Funded Study of Drill–in Fluids and Cleanup Methods," paper SPE 39473, presented at the 1998 SPE International Symposium on Formation Damage Control, Lafayette, Louisiana, Feb. 18–19.

Morganthaler, L. N. et al.: Optimization of Stimulation Chemistry for Openhole Horizontal Wells, paper SPE 49098, presented at the 1998 SPE Annual Technical Conference and Exhibition, New Orleans, Sep. 27–30.

Price–Smith, C. et al.: "Open Hole Horizontal Well Cleanup in Sand Control Completions: State of the Art in Field Practice and Laboratory Development," paper SPE 50673, presented at the 1998 SPE European Petroleum Conference, The Hague, The Netherlands, Oct. 20–22.

Donovan, J. P. and Jones, T. A.: "Specific Selection Criteria and Testing Protocol Optimize Reservoir Drill–in Fluid Design," paper SPE 30104, presented at the 1995 European Formation Damage Conference, The Hague, The Netherlands, May 15–16.

Fisk, J. V. and Shaffer, S. S.: "The Use of Filtration Theory in Developing a Mehanism for Filter–Cake Deposition by Drilling Fluids in Laminar Flow," SPEDE (Sep. 1991); 196–202.

Fisk, J., Guillory, J., and Morton, K.: "Minimizing Differential Sticking by Controlling Dynamic Filtration," paper presented at the 1992 American Association of Drilling Engineers Drilling Fluids Technology Conference, Houston, Apr. 22–23.

Fisk, J. V. and Jamison, D. E.: "Physical Properties of Drilling Fluids at High Temperatures and Pressures," SPEDE (Dec. 1989); 341–346.

Todd, B., and Murphy, R.: "Laboratory Device for Testing of Delayed Breaker Solutions on Horizontal Wellbore Filter Cakes," paper SPE 68968, presented at the 2001 SPE European Formation Damage Conference, The Hague, The Netherlands, May 21–22.

* cited by examiner

OIL WELL BORE HOLE FILTER CAKE BREAKER FLUID TEST APPARATUS AND METHOD

BACKGROUND OF THE INVENTION

1. Field of the Invention

The present invention relates to laboratory testing apparatuses and particularly to apparatuses and methods for determining the effectiveness and reaction time of an oil well bore hole filter cake breaker fluid.

2. Description of Relevant Art

Drilling fluid or drilling "mud" is used in drilling oil and gas wells to serve several purposes, including lubricating the drill bit, removing cuttings form the wellbore, and providing stability to the well. To accomplish its purposes, drilling fluid typically possesses several characteristics. One such characteristic is the ability if desired to form a coating or "filter cake" on the wall of the wellbore or borehole. The filter cake serves to stabilize the borehole and prevent loss of the liquid portion of the drilling mud through the walls of the borehole into the adjoining formations. This loss of liquid from the drilling mud, commonly referred to as fluid loss, is a function of many variables such as the composition of the drilling mud, the types of formations encountered in the drilling process, temperatures and pressure in the borehole, etc.

The ability to test drilling muds under simulated borehole conditions to determine characteristics such as fluid loss is desirable and apparatuses for such testing have been demonstrated. See for example, U.S. Pat. No. 4,748,849, issued Jun. 7, 1988 to Jamison et al. Commercial equipment is also available. Fann Instruments Company, a Halliburton Company, provides a Model 90, Dynamic Filtration Tester, that is particularly effective for dynamically measuring fluid loss characteristics.

Although a filter cake may be desirable during drilling a wellbore, removal of the cake is frequently desirable after the drilling is complete as the filter cake may interfere with production of oil and gas from the formation into the well. Thus, removal of filter cake from drilling fluids used to drill through producing zones of the formation is usually particularly desirable.

Many highly permeable, softer sandstone formations are completed with horizontal wellbores. These are generally open hole completions with screens, or screens-plus-gravel packs. The filtercake from the drilling fluid or "drill-in" fluid (as drilling fluids used for drilling through production zones may also be called) is left in place until after completion operations are finished. When the completion operations are done, a cleanup solution is pumped into the well to remove the filtercake from the wellbore face. These cleanup solutions can be, for example, acid, chelating agents, oxidizers, enzyme treatments, or combinations thereof A common disadvantage of any of these treatments is that the cleanup solutions tend to be highly reactive and may remove the filtercake at the point of circulation before the treatment can be placed over the entire open hole interval. This problem is especially common with clean-up solutions used to address the bridging particles used in payzone or "drill-in" fluids.

There is a need for cleanup solutions that have a delayed effect on filtercake integrity. Such delay allows the cleanup solution to be circulated across the interval before "leakoff," or before flow from a portion of the formation with filtercake removed occurs. Ideally, once the cleanup solution or filter cake breaker solution is in place in the wellbore, the cleanup solution begins reacting with the filtercake to remove it. If the delay could be made sufficiently long enough, the breaker solution could be placed with the gravel pack. Break time for this type application would need to be in the range of about four hours to as long as about twenty-four hours depending on the desire or need to have fluid loss control during subsequent pipe trips.

Conducting breaker tests for this type of delay could be extremely time consuming and prone to variations from test to test if conducted manually. Repeatability of the filtercake deposition becomes even more important when conducting sensitivity testing of the various components of a proposed cleanup solution. A need exists for automating filter cake construction and beaker solution testing.

SUMMARY OF THE INVENTION

For purposes of the present invention, known equipment for dynamically measuring fluid loss characteristics can be adapted to test filter cake breaker fluid. U.S. Pat. No. 4,748,849, for example, discloses an apparatus for dynamically testing fluid loss characteristics of a test fluid such as drilling mud. This apparatus comprises a filter medium cell with a generally vertically disposed, cylindrical wall section. The wall section has an inner surface and an outer surface. At least part and preferably all of the wall section is formed of a filter medium. A first chamber for a test fluid is in open communication with the inner surface of the cylindrical wall section of the cell. A second chamber is in open communication with the outer surface of the cylindrical wall section of the cell. A generally vertically disposed rotatable shaft is at least partially received in the filter medium cell and a rotator or other means is provided or included to rotate the shaft. The apparatus further includes a means to apply a differential pressure across at least a portion of the cylindrical wall section between the first chamber and the second chamber through the filter medium portion of the wall section. Means is also provided for measuring the amount of test fluid which passes from the first chamber to the second chamber through at least the filter medium portion of the wall section.

To adapt such an apparatus as disclosed in U.S. Pat. No. 4,748,849 for use in the method of the present invention, the apparatus is preferably fitted with a manual or automatic valve in the filter line to reduce the possibility of filter cake damage if and when the apparatus is opened. Also, preferably, a guide is added to prevent the shear shaft from damaging the filter cake if and when the shaft is removed after forming the filter cake.

In the method of the present invention, a dynamic filter cake is formed in such adapted apparatus of U.S. Pat. No. 4,748,849 or similar apparatus capable of forming a filter cake with drilling mud at a desired temperature and differential pressure, such as a temperature and pressure expected to be encountered in a subterranean wellbore. Filter cake breaker fluid is then substituted in the apparatus in place of the drilling mud. Such substitution may typically be effected by opening the apparatus and removing the drilling mud, by for example pouring the drilling mud out and replacing it with breaker fluid, or by for another example allowing the drilling mud to drain out into an auxiliary fluid container and adding the breaker fluid from another auxiliary fluid container, preferably without having to depressurize or cool the apparatus system. Collection of filtrate is begun, resumed or continued (filtrate likely having been collected during formation of the filter cake), and the quantity may be monitored over time. An increase in the filtration collection rate indicates filter cake removal. The greater the increase or rate of change, and the faster the flow of fluid, the greater the degree of filter cake removed.

DETAILED DESCRIPTION OF PREFERRED EMBODIMENTS

Figure 1:
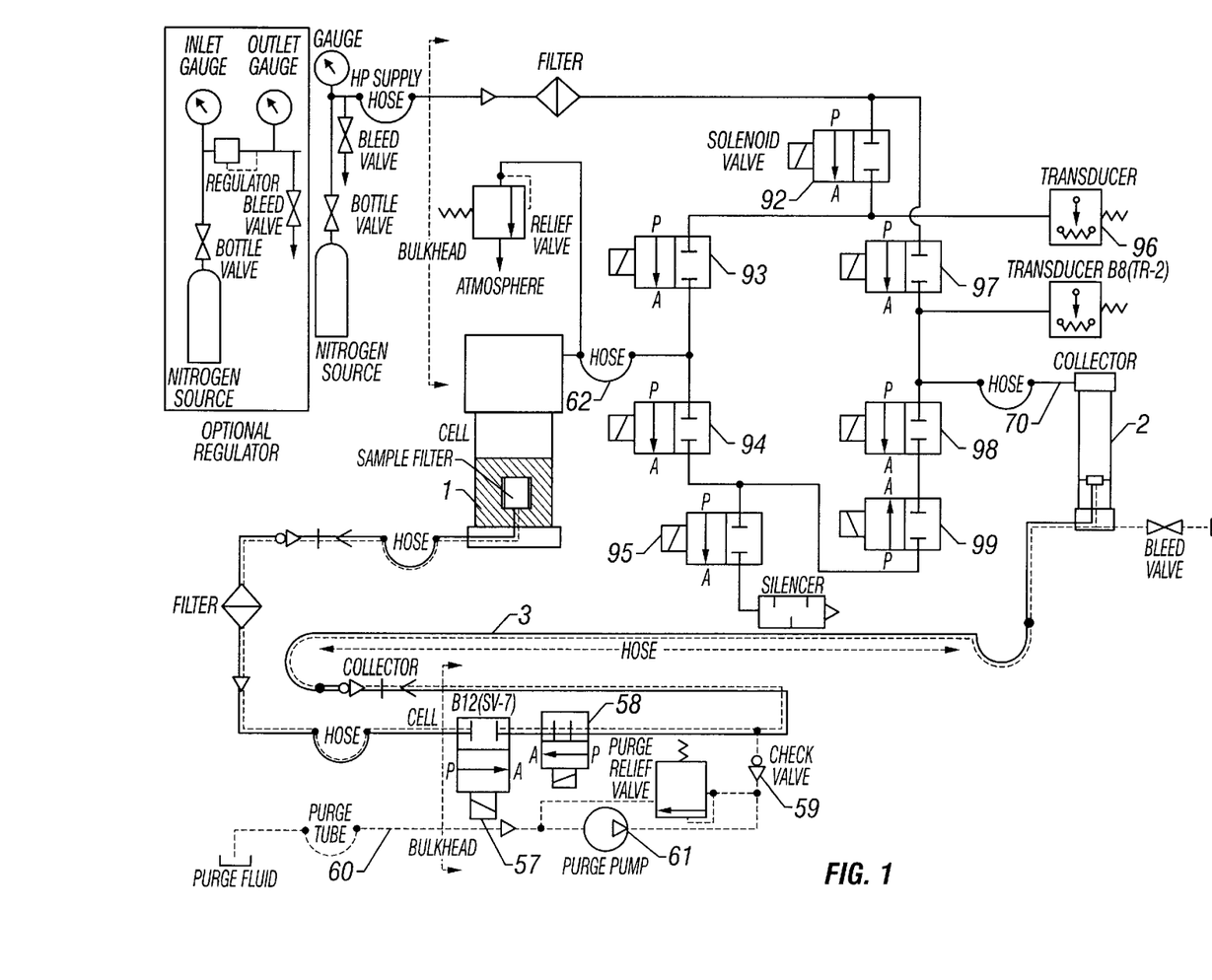
FIG. 1 is a diagrammatic view of an apparatus of the invention, suitable for use in the method of this invention, parts of the apparatus being shown in elevated cross section.

Referring to FIG. 1, an apparatus suitable for use in the method of the present invention is comprised of two main components—a filtration unit 1 and a measuring unit 2. Units 1 and 2 are connected by a line 3 which provides fluid communication, in a manner described hereafter, between the filtration unit 1 and the measuring unit 2.

Figure 2:
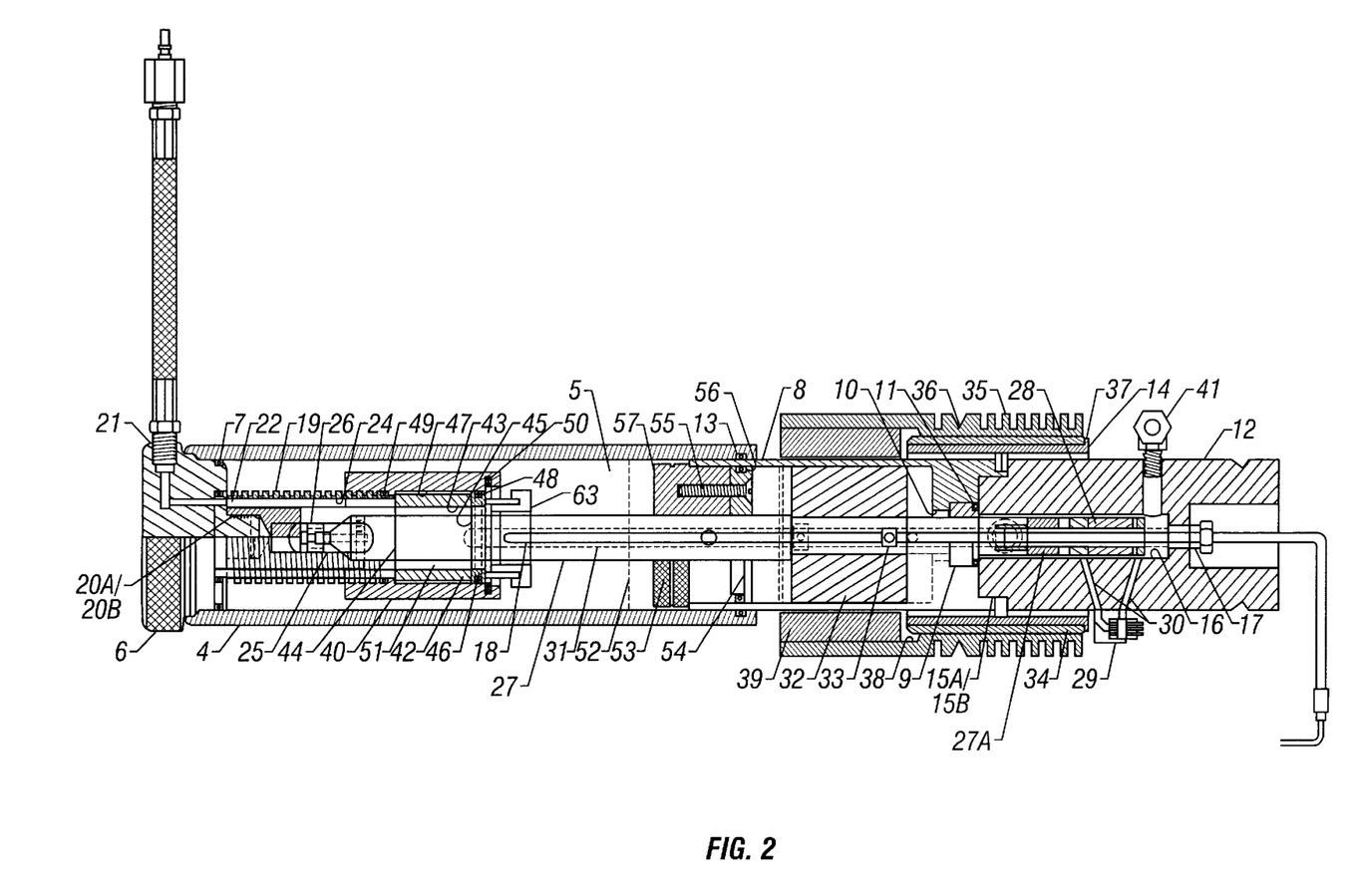
FIG. 2 is an elevated view, partly in section, of the filtration unit of the apparatus of FIG. 1.

Referring to FIG. 2, the filtration unit 1, also shown in FIG. 1, includes a generally cylindrical, vertically disposed housing 4 partially defining an interior chamber 5. A heating jacket (not shown) surrounds housing 4 such that housing 4 and anything therein can be raised to a desired temperature. Chamber 5 is also partially defined by a generally cylindrical cap 6, which is received in the open end of housing 4. To effect a seal between cap 6 and housing 4, thereby effectively sealing off chamber 5, an O-ring 7 is provided. O-ring 7 is carried in an annular groove formed on the exterior surface of cap 6. To secure cap 6 to housing 4, threads in the cap 6 engage threads of housing 4.

The chamber 5 is further defined by a generally cylindrical housing 8. Housing 8 is received in the open end of housing 4. To effect a seal between housing 4 and housing 8, an O-ring 13 is provided. O-ring 13 is carried in an annular grooved formed on the interior surface of housing 4. Housing 8 is made of a high strength non-magnetic material so that it offers minimum resistance to magnetic fields. One example material suitable for comprising housing 8 is metal alloy UNS N05500, available from many sources. Other non-magnetic materials could be used, even for example plastic or fiberglass. A bore 10 with a plurality of diameters extends through the housing 8, providing a position for bearing 9, and extending chamber 5. An annular groove in the exterior surface of bearing 9 restrains an O-ring 11, which seals the radial joint between housing 8 and housing 12. The end of housing 12 that is connected to housing 8 is provided with male threads 15a, which engage matching female threads 15b in housing 8.

A plurality of threaded ports are positioned in housing 12 to provide communication means to chamber 5 via bore 16 in housing 12. One of those ports is positioned on the axial centerline of housing 12, and is threaded to receive a seal 17. Seal 17 holds a temperature probe 18 for determining the temperature of the fluids in the chamber 5 by electronic means. Temperature probe 18 could be of the thermocouple or RTD type, and extends along the centerlines of housings 12, 8 and 4 into housing 4, below the level to which a liquid sample would be poured into chamber 5. A fitting 41 connects to a fluid conduit that leads to a controlled source of pressurized gas (not shown). Pressure can be applied through fitting 41 to pressurize the interior chamber 5.

A generally cylindrical support 19 connects on the axial centerline to cap 6, by means of female threads 20a in the end and matching projecting male threads 20b on the cap 6. Fluid communication through port 21 to the top of support 19 is enabled by means of bores 22 of varying length and diameters. O-ring 23, in a radial groove in cap 6, around the end of the support 19, seals chamber 5 from the bores 22. The outside cylindrical surface of the support 19 has a course male thread. A bore 24, partially through the centerline of support 19, and an intersecting slot 25 through support 19, provides access to a bearing 26. In the preferred embodiment of this invention, the bearing is a miniature angular contact ball bearing, but other type bearings could be used.

Hollow cylindrical filter medium 42 is held tightly in the axial direction in filter holder 40. The inner surface of the filter medium wall 43 and the outer surface of a general cylindrical shaft 27 with a plurality of diameters form a uniform cylindrical annular gap 51 that communicates directly with chamber 5. At least a portion, and preferably all, of the wall 43 of filter medium 42 is formed of a material which is at least partially permeable to liquids. Such materials include, without limitation, sintered metals, layered screens, natural mineral materials, synthetic materials, etc. The inner bore 47 of filter holder 40, which is generally cylindrical, is sized to snugly receive filter medium 42. This forms an annular gap between the filter medium 42, and the inner bore 47 of the filter holder 40. An annular seal 44 effects a seal between the lower end of filter medium 42 and the top of support 19. A similar annular seal 45 effects a seal between the top end of filter medium 42 and the generally cylindrical retainer 46. Retainer 46 is held in place by retaining ring 50, in a groove in the top of the filter holder 40. An O-ring 48, retained in a groove in the outer surface of retainer 46, effects a seal between the retainer 46 and the smooth inner bore 47 of filter holder 40. Similarly, O-ring 49, retained in a groove in the outer surface of the upper end of support 19, effects a seal between the smooth inner bore 47 of filter holder 40 and the top end of support 19. By screwing the filter holder 40 onto support 19, axial force is applied to seals 44 and 45, effectively isolating the annular space at the inner bore 47 from communication with chamber 5, except through filter medium 42. However, the annular space at the inner bore 47 is connected to port 21 through bores 22 and a small cross-bore (not shown) in support 19, above O-ring 49. Therefore, if chamber 5 is filled to a level 52 above the filter medium 42 with a test liquid, and it is pressurized with gas introduced through fitting 41 into the upper portion of chamber 5, the test liquid will be forced radially through the filter medium 42. The test liquid will then flow into the annular space at the inner bore 47 of the filter holder 40, and conducted to port 21. The rate at which the test liquid flows through the filter medium 42 will be a function of the permeability of the filter medium 42, the pressure difference between chamber 5 and port 21, the viscosity of the liquid, the tendency of the components of the test liquid to plug the pores of the filter medium 42, and the time that it flows.

Bearing 26 supports and accurately centralizes one end of shaft 27. Shaft 27 is supported at the upper end by radial bearing 9. In the preferred embodiment, shaft 27 is made up of two components, connected by means of axial threads. Shaft 27 has a bore 31 partially through its length, along its centerline. Bore 31 provides clearance so that shaft 27 can be rotated about the stationary temperature probe 18, which extends down the center of the bore when the shaft is installed. Shaft 27 can be removed or installed as determined by the needs of the test.

Shaft 27 is driven magnetically by means of a generally rectangular magnetically soft rotor 32. A bore through rotor 32 allows it to receive shaft 27, which passes through it. Rotor 32 is secured to the shaft 27 by means of a threaded set screw 33, which engages a flat on the outer surface of shaft 27. The rotor is sized so that when it rotates it just clears the inside surface of housing 8 with the minimum practical gap. Thus, shaft 27 can be rotated inside of chamber 5 without the use of dynamic seals.

The upper section of shaft 27 carries a plurality of permanent magnets 28, equally spaced about the outer surface of shaft component 27a, such that when the shaft is rotated, a rotating magnetic field is created. The rotating magnetic field can be detected by electronic means, to measure the rotation rate of the shaft. In the preferred embodiment of this invention, a Hall effect device 29 is used to detect the rotating magnetic field of shaft 27. The magnetic field is conveyed to the Hall effect device 29 by means of at least two magnetically soft rods 30 that fit into bored holes in housing 12, forming a magnetic circuit. The bored holes that receive rods 30 penetrate close to bore 16 but do not enter it. This allows detection of the rotational speed of shaft 27 without the use of seals. The housing 12 and upper shaft component 27a must both be made of a non-magnetic material to prevent the dissipation of the shaft 27's rotating magnetic field. One example material suitable for comprising the housing 12 and shaft component 27a is metal alloy UNS N05500, available from many sources. Other non-magnetic materials could be used, even for example plastic or fiberglass.

Also threaded to the male thread of housing 12, by means of a web in the gap between housings 8 and 12 is a generally cylindrical bearing journal 14 of various diameters. Bearing journal 14 supports a bearing bushing 34 on a stepped increase in the diameter of the outer surface of bearing journal 14, which acts as a thrust bearing. Bearing bushing 34 is tightly received into a bore in generally cylindrical magnetic rotor 35, so that it turns with the magnetic rotor 35. Magnetic rotor 35 is comprised of a magnetically soft material such as low carbon steel, so that it may convey magnetic fields. Retaining ring 37 prevents upward motion of magnetic rotor 35 on bearing journal 14. A large bore in the bottom end of magnetic rotor 35 positions two magnets 39 so that when magnetic rotor 35 is rotated, the magnets 39 just clear housing 8. This minimizes the gap between the magnets 39 and the shaft rotor 32, so that a strong magnetic field can be conveyed between them for maximum torque transmission. The two magnets 39 are positioned diametrically opposed in shallow grooves in the inside surface of bore 38. A V-belt groove 36 in the outside surface of magnetic rotor 35 is used to drive the magnetic rotor 35, turning the shaft 27 at any desired rotational speed.

As earlier noted, chamber 5 is heated by means of a jacket (not shown) to allow test fluid in chamber 5 to be maintained at any desired temperature. The gas space in chamber 5, above the fluid level 52, is separated into two sections, in communication with each other, by means of the generally cylindrical bulkhead assembly 57. Bulkhead assembly 57 is made up of bulkhead 53 and O-ring holder 54. A plurality of screws 55 holds bulkhead 53 and O-ring holder 54 together. Bulkhead 53 is made of a material of low thermal conductivity, in this case, a plastic. O-ring 56, retained in a groove in the exterior surface of O-ring holder 54, is used to retain the bulkhead assembly 57 in place by means of friction with the inner surface of housing 8. A bore through the center of bulkhead assembly 57 provides minimal clearance around shaft 27 so that shaft 27 can turn freely. Bulkhead assembly 57 provides a means of minimizing the transfer of heat to the upper, unheated sections of chamber 5.

In use, the vertically disposed assembly of housings 4, 8 and 12 is restrained from separating, under the influence of elevated pressures in chamber 5, by means of a substantially rigid yoke (not shown). Suitable hinges and brackets (not shown) allow the assembled housings 4, 8 and 12 to be pivoted from the vertical position so that cap 6 clears the yoke (not shown) and the housings 4 and 8 can be separated.

Figure 3:
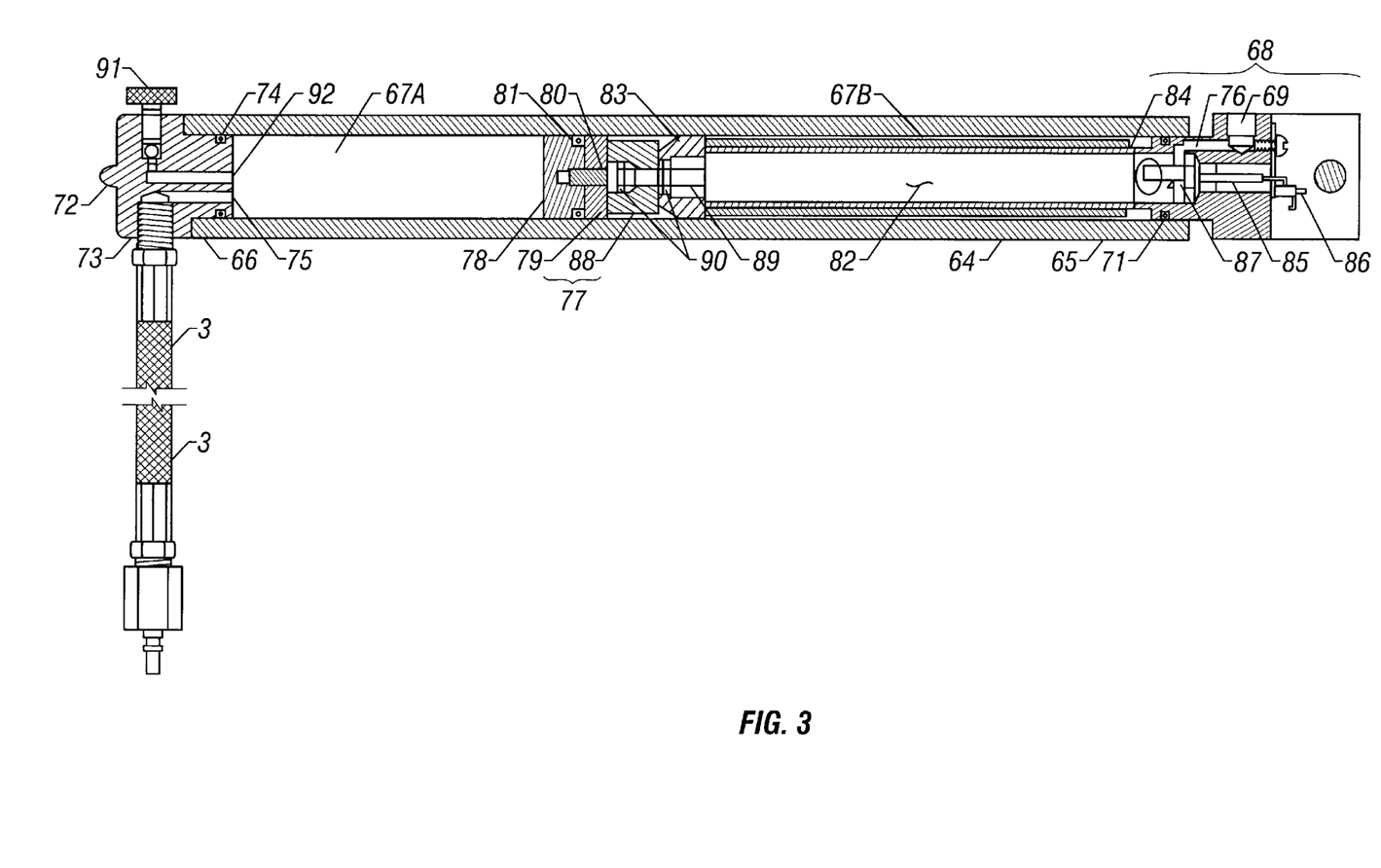
FIG. 3 is an elevated view, partly in section, of the measuring unit of the apparatus of FIG. 1.

As earlier noted, the annular space at the inner bore 47 of filter holder 40 is in open communication with port 21 by means of bore 22. Conduit or line 3 is also in open communication with port 21 and with measuring unit 2 via solenoid valve 57. Referring to FIG. 3, a solenoid valve 58 is preferably inserted in line 3 to reduce the possibility of filter cake damage (at least to reduce damage below a significant degree or amount, i.e. an amount that might change test results or alter conclusions regarding the performance or effectiveness of a breaker fluid being tested according to the method of the invention) if the filtration unit 1 is opened to remove drilling mud.

Also connected to line 3 through check valve 59 and pump 61 is a conduit 60 leading to a source of cold purge liquid. Referring to both FIGS. 2 and 3, if pressure is applied to chamber 5 via conduit 62, with a drilling liquid or mud received in chamber 5, mud permeating through the wall 43 of the filter medium 42 will enter annular space 47, i.e., the mud will pass from chamber 5 to chamber annular space 47, and will then be forced down bore 22, out port 21 into line 3 through valve 57 and added valve 58 and into measuring unit 2. A filter cake will form on the filter medium wall 43.

An optional guide 63 preferably positioned along the path of shaft 27 will allow removal of the shaft preferably with minimal disturbance of such filter cake. Shaft 27 is preferably removed for static testing of filter cake breaker fluids, according to the method of the invention.

Referring to FIG. 3, the measuring unit 2, also shown in FIG. 1, is shown in greater detail. Measuring unit 2 comprises a generally vertically disposed cylindrical tube 64 having a first end 65 and a second end 66 defining a piston chamber 67. Received in the first end 65 of tube 64 is a first plug 68 having a side, fluid port 69 whereby a tubing fitting or the like can be received to connect port 69 through conduit 70 to a source of pressurized gas. A bore 76 allows gas communications between port 69 and upper piston chamber 67b. An O-ring 71 provides sealing between plug 68 and tube 64. A second plug 72, having a fluid port 73, is received in the second end 66 of tube 64. A bore 75 in second plug 72 allows fluid communications between port 73 and the lower chamber 67a. An O-ring 74 provides sealing between tube 64 and plug 72. A purge valve 91, connected to chamber 67 by a bore 92, in conjunction with purge pump 61, is used to flush air out of the lower piston chamber 67a, when the piston is in the fully downward position.

A piston assembly shown generally as 77 in the fully upward position, is slidably mounted internally of tube 64. Piston assembly 77 comprises a piston cap 78 which is secured to a piston head 79 by means of a screw 80 received in a threaded bore in the piston cap 78 of piston 77. Piston head 79 is made of a magnetic material, preferably a magnetic type stainless steel. An annular seal ring 81 provides sealing between the tube 64 and the piston cap 78 of piston 77 thereby dividing chamber 67 into two separate chambers 67a and 67b.

A generally cylindrical, linear variable resistor 82 is rigidly held in a central bore of first plug 68 by means of resistor holder 83, which screws onto a male threaded projection 84 of first plug 68. A three conductor electrical feed-through 85. is received in a central bore in first plug 68. The feed-through provides a high pressure gas seal with three isolated electrical conductors passing through it. Connector 86 provides means to connect the three conductors to a substantially constant voltage source and electronic circuits that measure voltage (not shown). Connector 87 provides means to connect the electrical wires of the linear variable resistor 82 to the electrical feed-through 85.

A magnet 88 is rigidly attached to the threaded shaft 89 of linear variable resistor 82, passing through a central bore in magnet 88, by means of nuts 90. Magnet 88 magnetically attaches to the magnet piston head 79 of piston assembly 77. As the piston assembly 77 moves in the bore of tube 64, it changes the position of the shaft of the linear variable resistor 82, so that the resistance of the variable resistor 82 is substantially proportional to the vertical position of the piston assembly 77. With a substantially constant voltage applied to the ends of the linear variable resistor 82, the resistance change is converted to a variable voltage. With proper calibration, the position of the piston assembly 77 can be accurately correlated with the voltage from the linear variable resistor 82. By this means, the position of the piston assembly 77 can be externally determined and recorded. Since the diameter of the bore of cylinder 64 is known, the instantaneous position of the piston assembly 77 can be used to calculate the volume of chamber 67a. The voltage signal from linear variable resistor 82 is sent to a digital computer, which records and displays the volume displacement of piston assembly 77 as a function of time.

Referring to FIGS. 1 and 3, automatic coordinated operation of solenoid valves 92, 93, 94 and 95 provides pressurized gas, usually nitrogen, to line 62 to adjust and maintain the pressure in chamber 5. This pressure is detected by means of sensor 96. The pressure in the piston chamber 67 of the measuring unit is controlled to be less than or equal to the pressure of chamber 5 by means of solenoid valves 97, 98, 99 and 95, through line 70. The pressure supplied to piston chamber 67 is measured by means of sensor 97.

Referring to FIGS. 1, 2, and 3, in operation for effecting the method of the invention, a filter medium 42 is placed in filter holder 40. Housing 4 is then screwed onto cap 6. Fluid line 3 is connected to the filter or filtration unit 1 and the measuring unit 2 and the purge pump 61 is run to flush air out of the system. At the same time, in measuring unit 2, piston assembly 77 is positioned such that the cap 78 is against plug 72, i.e., so that there is no displaced volume in tubular cylinder 64, and chamber 67a is essentially of zero volume. After purging, the used purge liquid is poured out of the chamber 5 and replaced with drilling fluid to level 52. The filtration unit is sealed by assembling the lower portion of the unit to the upper at the junction between housing 4 and 8. The filtration unit 1 is then rotated to the vertical position so that it engages the previously noted yoke (not shown) at the top and bottom of the filtration unit. After the heating jacket (not shown) is closed around housing 4 (assuming heating is desired), the dynamic filtration system is ready to run.

The motor (not shown) which drives the magnetic rotor 35 is started to impart rotation to shaft 27 at a pre-selected, constant speed. If desired, the filtration unit 1 is heated to a predetermined elevated temperature using the heating jacket around housing 4 (not shown). To control the pressure in chamber 5, solenoid valves 92, 93, 94 and 95 are opened and closed in a coordinated manor to incrementally raise or lower the pressure through line 62. At the same time, the operation of solenoid valves 94, 95, 98 and 99 are coordinated so that the pressure in the upper chamber 67b of the measuring unit 2 is kept equal to the pressure in chamber 5. Under theses conditions, piston assembly 77 will be held in position by pressure equal to the difference between the pressure in chamber 5 and the pressure in piston chamber 67b exerted by pressurized gas from line 70. This arrangement permits virtually unlimited control of the differential pressure across the wall 43 of the filter medium 42.

When the test conditions have been reached, the valves 94, 95, 98 and 99 are coordinated so that the pressure in the upper chamber 67b of the measuring unit 2 is incrementally reduced until the desired pressure differential between chamber 5 and chamber 67b has been established. At this point, filtrate solenoid valves 57 and 58 are opened. Since the pressure in chamber 5 will always be greater than the pressure in chamber 67b, and depending upon the permeability of the filter medium and the nature of the drilling mud, etc., fluid will flow through the permeable filter medium out of chamber 5 via the clearance or annulus 51 between shaft 27 and the radially inner surface 43 of filter cell medium 42. The drilling mud will then pass into the annular space at the inner surface 47 of the filter holder 40, through bore 22, and will exit the filtration unit 1 via port 21 and line 3 through open solenoid valves 57 and 58 and finally through port 73 in plug 72 into chamber 67a adjacent end 66 of the measuring unit 2. Drilling mud entering chamber 67a will displace piston assembly 77 away from end 72 toward end 65. As this occurs, the resistance of the variable linear resistor 82 changes as a function of the volume of filtrate being accumulated in the chamber 67a. This accumulated volume, initially read as a voltage, is then conveniently recorded as volume measurement versus time by the control computer. With these values, the flow rate of drilling mud through the filter medium can be easily computed. A reduction in flow rate indicates a filter cake has formed on the surface 43 of the filter medium 42.

Once a filter cake has formed, breaker fluid is substituted for the drilling mud in the apparatus. Such substitution may be accomplished by opening the apparatus and pouring out the drilling mud (and pouring in the breaker fluid), or more preferably without altering the pressure in the apparatus, by allowing the drilling fluid to drain out preferably under the forces of gravity, and the breaker fluid to drain in (from an auxiliary container) also preferably under the force of gravity. In the case where the apparatus is opened, the shaft 27 will be removed from the center of the filter medium 42, guided by guide 63, preferably without disturbing the filter cake (or without damaging it to a significant degree, i.e., to an amount affecting the flow rate such that test results may be changed). Monitoring the flow rate of fluid—now breaker fluid instead of drilling mud—across the filter medium is continued or resumed under static conditions (i.e., without shearing).

This apparatus is useful for simulating shearing similar to that which drilling mud would undergo when in actual use in a drilling operation. The annulus 51 simulates the annulus which would exist between a conventional drill string and the wall of a borehole during a drilling operation. As shaft 27 is rotated at any desired rate, the drilling mud in the annulus 51 sees a shearing action, which is a function of that rotational rate. The shear rate may be varied widely by virtue of the fact that not only can the shaft rotational speed be varied but the radial size of the annulus 51 can also be varied by changing the diameter of the lower portion of shaft 27.

Another feature of this apparatus is that the surfaces of the filter medium, which are exposed to the drilling mud and to the breaker fluid, are oriented in a generally vertical direction. Accordingly, settling out of solids, e.g., filter loss additives in the drilling mud, will not add to the filter cake. This feature is particularly important in static testing of the breaker fluid (i.e., when the shearing shaft 27 is not used or not rotated.) Moreover, the generally vertical orientation of the filter medium and its coaxial relationship to the shaft 27 simulates the geometry of an actual well.

The simplified construction of this apparatus allows the filter medium to be changed and made from a variety of materials to simulate downhole formations.

Experimental

A breaker fluid was tested for producing a break in the range of about 10 to about 16 hours to allow breaker fluid placement with the gravel pack and enough time to remove the service tool from the well. An oxidizing breaker was chosen, for which a low-reactivity, low-temperature activator was available.

The following testing procedure was used:

1. The drilling fluid to be tested was prepared as set forth in Table 1 and hot rolled for 16 hours;
2. The filter core was assembled into the coreholder of the apparatus of the invention with the shaft guide;
3. The drilling fluid was loaded into the apparatus of the invention for filter-cake formation, according to the steps set forth in Table 2,
4. Testing was done to verify the filter cake was formed satisfactorily;
5. The drilling fluid was poured off,
6. The cell and coreholder were rinsed without disturbing the filter cake;
7. The breaker fluid to be tested (11.5 lb/gal NaCl/NaBr brine plus oxidizer/activator) was loaded into the apparatus of the invention; and
8. The breaker fluid test was conducted according to the sequence set forth in Table 3.

TABLE 1

Drill-In Formula Used During Delayed-Breaker Tests

| Component | Amount |
|---|---|
| Water | 0.465 bbl |
| 12.3 lb/gal. NaBr Brine | 0.465 bbl |
| NaCl | 56.5 lb |
| KCl | 7.1 lb |
| Xanthan | 1.25 lb |
| Starch | 7.0 lb |
| CaCO$_3$ 5-micron | 10.0 lb |
| CaCO$_3$ 25-micron | 25.0 lb |
| NaOH | 0.1 lb |
| Rev Dust | 20.0 lb |

TABLE 2

Sequence for Filter Cake Formation

| Step No. | 1 | 2 | 3 | 4 | 5 | 6 |
|---|---|---|---|---|---|---|
| Time (min) | 0 | 0 | 2 | 60 | 15 | 0 |
| Static Pressure (psi) | 800 | 800 | 800 | 800 | 800 | 0 |
| Differential Pressure (psi) | 0 | 500 | 500 | 500 | 500 | 0 |
| Temperature (° F.) | 132 | 132 | 132 | 132 | 132 | 115 |
| Shear Rate (1/sec) | 100 | 100 | 100 | 100 | 10 | 0 |
| Filtrate Valve | Off | Off | Off | On | On | Off |

TABLE 3

Sequence for Delayed Filter Cake Break

| Step No. | 1 | 2 | 3 | 4 | 5 | 6 |
|---|---|---|---|---|---|---|
| Time (min) | 0 | 0 | 2 | 999 | 999 | 0 |
| Static Pressure (psi) | 800 | 800 | 800 | 800 | 800 | 0 |
| Differential Pressure (psi) | 0 | 50 | 50 | 50 | 50 | 0 |
| Temperature (° F.) | 132 | 132 | 132 | 132 | 132 | 115 |
| Shear Rate (1/sec) | 0 | 0 | 0 | 0 | 0 | 0 |
| Filtrate Valve | Off | Off | Off | On | On | Off |

Figure 8:
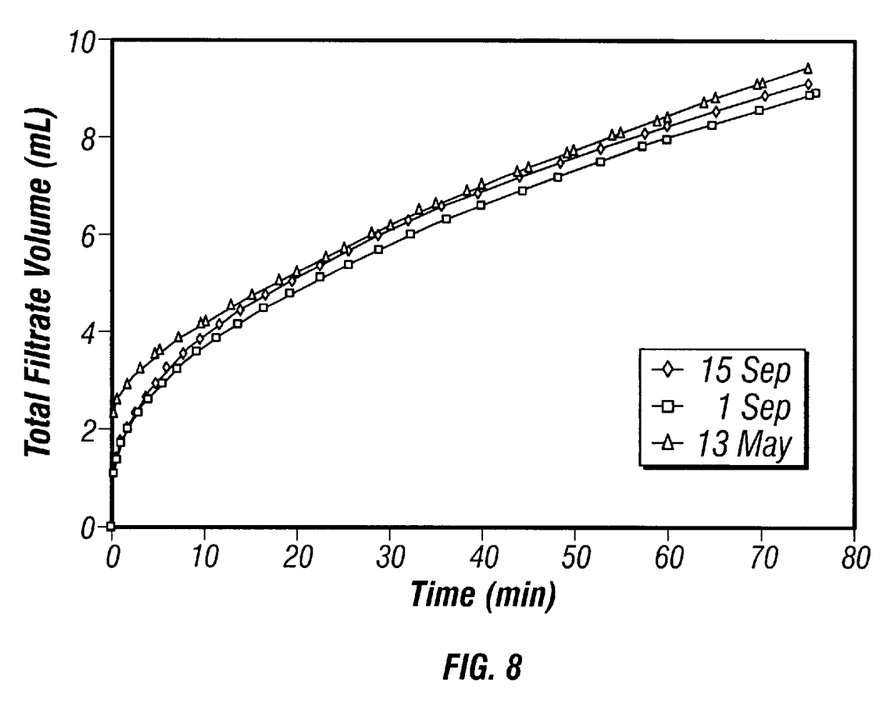
FIG. 8 is a graph comparing dynamic cake deposition.

Further with respect to Step 4 above, an example of a way to test for satisfactory formation of filter cake is by comparing the filter profile to others for the drilling fluid recipe. The filter profile is the curve of the filtrate versus time during dynamic filtration and cake deposition. When the same drilling fluid recipe is used, the filter profile should match. As shown in FIG. 8, tests performed several months apart still produced nearly identical curves. The slope of the curve at the latter part of the test indicates the thickness and permeability of the filter cake when the same viscosity fluid was used under the same differential pressure. The ability to obtain a particular filter-cake thickness is a result of a balance being reached between deposition and erosion forces. The filter-cake thickness will increase until shear forces on a particle at the surface of the filter cake are strong enough to overcome the forces acting on the particle to keep it in place (particle-to-particle attraction and viscous drag from leakoff). The filter cake will maintain this thickness as long as the imposed-shear and differential-pressure conditions do not change. Testing the same fluid under the same conditions results in repeatable and uniform filter cakes.

Figure 4:
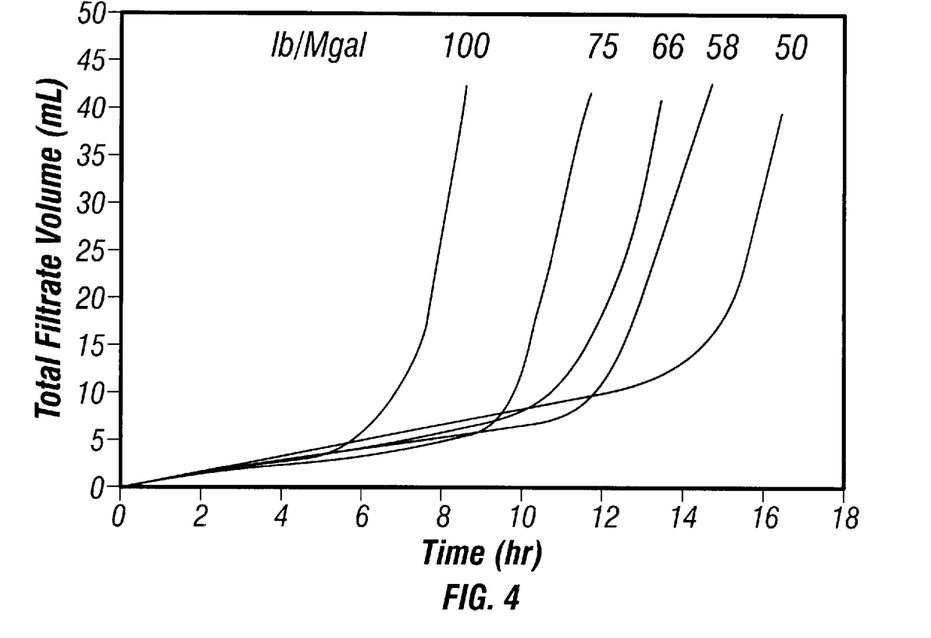
FIG. 4 is a graph showing filter cake break time versus breaker fluid concentration in a test example of the method of the invention using the apparatus of FIG. 1 at 132 degrees Fahrenheit, 50-psi differential pressure, and 11.5 lb/gal. NaCl brine.
Figure 5:
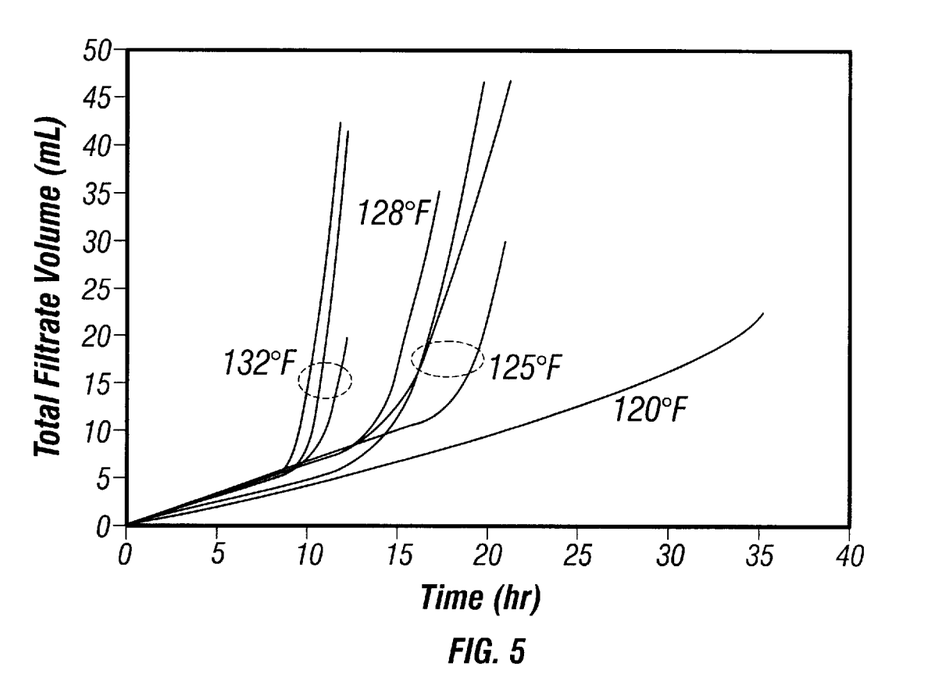
FIG. 5 is a graph showing filter cake break time versus temperature in a test example of the method of the invention using the apparatus of FIG. 1 at 50-psi differential pressure, 11.5 lb/gal. NaCl/NaBr brine.
Figure 6:
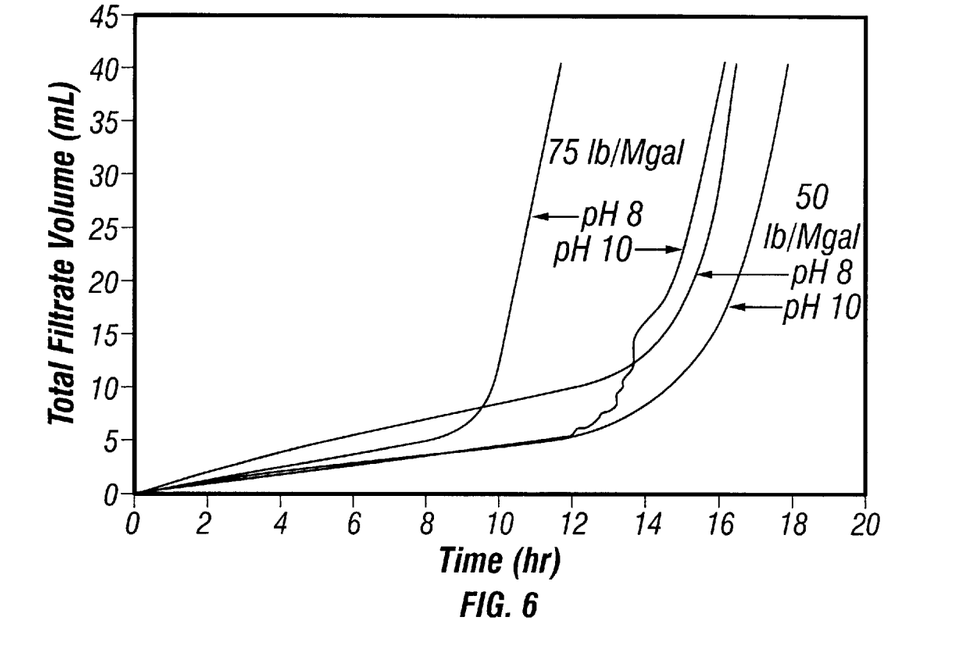
FIG. 6 is a graph showing filter-cake break time versus pH in a test example of the method of the invention using the apparatus of FIG. 1 at 132 degrees Fahrenheit, 50-psi differential pressure, 11.5 lb/gal. NaCl/NaBr brine.

Producing a series of essentially identical filter cakes and repeating the breaker fluid tests enables testing of the effects of even slight changes to the testing parameters. FIG. 4 shows the effect of the breaker fluid concentration on break time. FIG. 5 shows, for a particular breaker fluid concentration, the effect of wellbore cool-down during gravel pack treatment. Three tests each were run at two of the temperatures, as shown, with very good agreement in break times. Another example, shown in FIG. 6, gives the results at two breaker concentrations in which the effect of pH was tested.

Figure 7:
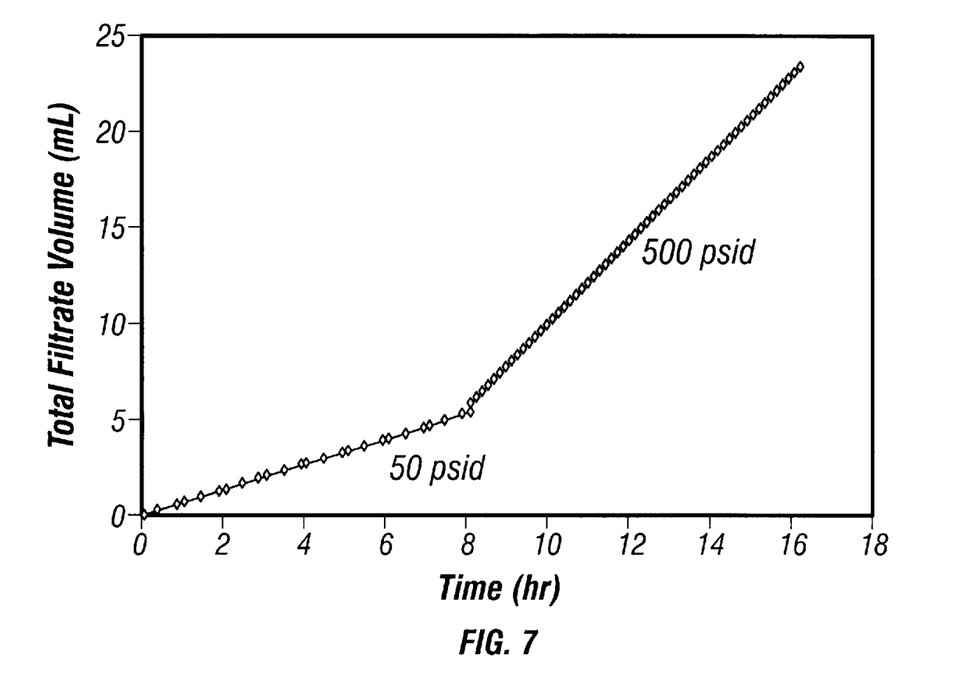
FIG. 7 is a graph showing use of the apparatus of FIG. 1 for filter-cake diagnostic testing.

The apparatus of the invention can also be used to perform diagnostic testing on the properties of a filter cake. FIG. 7 shows the results of a "blank" breaker fluid test in which the base brine, without the oxidizer, was tested. After 8 hours, the differential pressure across the filter cake was increased from 50 to 500 psi. The leakoff rate did not increase by a factor of 10. This occurred because the filtercake was compressible, and the permeability was decreased by increased differential pressure. This test may also be performed to confirm that the breaker fluid curves are showing an actual break of the filter cake and not the flushing of polymers from the filter cake. The straight lines in FIG. 7 indicate that the filter cake was not being degraded as a result of brine being pumped through it.

As these experiments indicate, delayed breaker fluid testing is preferably done by repeating the test using several filter cakes with the same thickness and properties and then comparing the filter profiles for several separate test runs.

The foregoing description of the invention is intended to be a description of preferred embodiments. Various changes in the details of the described method and apparatus can be made without departing from the intended scope of this invention as defined by the appended claims.

We claim:

1. A method for testing the effectiveness or reaction time of a breaker fluid in breaking a filter cake on sides of a borehole penetrating a subterranean formation, said method comprising:
   (a) obtaining an apparatus comprising a filter medium and the capability of facilitating formation of a repeatable and uniform filter cake on a filter medium under dynamic or static conditions and of allowing monitoring of fluid passing through said filter medium;
   (b) positioning a drilling mud in said apparatus capable of forming a filter cake on said filter medium of said apparatus under imposed-shear and differential pressure conditions;
   (c) forming a filter cake on said filter medium while controlling imposed-shear and differential pressure conditions;
   (d) substituting said breaker fluid for said drilling mud in said apparatus; and
   (e) monitoring the amount of breaker fluid that passes through said filter medium under, static conditions over time and determining the instantaneous rate of filtration.

2. The method of claim 1 wherein said substitution of breaker fluid for drilling mud is effected without significant damage to the filter cake and without altering the pressure in the apparatus.

3. The method of claim 1 wherein said filter medium of said apparatus comprises a filter medium cell having a generally vertically disposed cylindrical wall with an inner surface and an outer surface such that at least a portion of said cylindrical wall is formed of said filter medium, and wherein said filter medium may be changed to simulate different downhole formations.

4. The method of claim 3 wherein said apparatus further comprises:
   (a) a first chamber for said test fluid in open communication with the inner surface of said cylindrical wall;
   (b) a second chamber in open communication with the outer surface of said cylindrical wall;
   (c) a generally vertically disposed rotatable shaft, at least a portion of which is received in said filter medium cell, generally surrounded by said cylindrical wall; and
   (d) a rotator for said rotatable shaft for imparting shear in said drilling mud in forming said filter cake.

5. The method of claim 1 wherein said filter cake is formed on said filter medium by applying a differential pressure across said filter medium.

6. The method of claim 4 wherein said apparatus further comprises a monitor for monitoring the flow of fluid across said filter medium.

7. The method of claim 5 wherein said apparatus further comprises a shaft which facilitates application of shear to said drilling mud when forming said filter cake.

8. The method of claim 7 further comprising removing said shaft after formation of said filter cake and before or at about the time of substitution of said breaker fluid for said drilling mud.

9. The method of claim 8 wherein said apparatus further comprises a guide in association with said shaft such that removal of said shaft from said apparatus does not significantly affect said filter cake.

10. The method of claim 8 wherein said apparatus further comprises at least one valve in or associated with said filter medium such that said filter cake is not significantly damaged if said apparatus is opened.

11. The method of claim 5 wherein substitution of breaker fluid for drilling mud is accomplished by draining said drilling mud out of said apparatus and adding said breaker fluid to said apparatus without depressurizing said apparatus.

12. The method of claim 11 wherein auxiliary fluid containers are used to receive said drilling mud and to dispense said beaker fluid to said apparatus during said substitution of breaker fluid for drilling mud.

13. The method of claim 12 wherein said draining of drilling mud is effected by gravity.

14. The method of claim 12 wherein said dispensing of said breaker fluid into said apparatus is effected by gravity.

15. The method of claim 1 wherein said substitution of breaker fluid for drilling mud is effected by pouring said drilling mud out of said apparatus.

16. The method of claim 6 wherein said monitoring is accomplished automatically.

17. The method of claim 16 wherein said automation is effected with a computer.

18. The method of claim 17 wherein said computer is programmed to record quantity of fluid passing across said medium at periodic intervals.

19. The method of claim 1 wherein said apparatus comprises at least one part or mechanism that protects or prevents significant damage to said filter cake when said breaker fluid is substituted for said drilling mud.

20. An apparatus for testing the effectiveness of a breaker fluid in breaking a filter cake on the wall of a borehole penetrating a subterranean formation, said apparatus comprising:
   (a) a filter medium cell having a generally vertically disposed cylindrical wall with an inner surface and an outer surface such that at least a portion of said cylindrical wall is formed of a filter medium;
   (b) a first chamber for said fluid in open communication with the inner surface of said cylindrical wall;
   (c) a second chamber in open communication with the outer surface of said cylindrical wall;

(d) a generally vertically disposed, removable, rotatable shaft, at least a portion of which is received in said filter medium cell, generally surrounded by said cylindrical wall;

(e) a rotator for said rotatable shaft for imparting shear to fluid;

(f) means for forming a repeatable, uniform filter cake on said filter medium under controlled shear and differential pressure;

(g) a piston and associated means for instantaneously monitoring the amount of fluid that passes through the filter medium as a function of time;

(h) means for changing fluids in said first chamber; and (i) means for removing said shaft without significantly disturbing filter cake on said filter medium.

21. The method of claim 6 wherein said monitor comprises a piston and means for correlating the displacement of said piston with the filtration rate.

22. The method of claim 1 wherein said filter medium is changeable.

23. The apparatus of claim 20 wherein said monitoring is facilitated with means for detecting movement of said piston indicating change in fluid volume and flow rate through the filter medium.

* * * * *